United States Patent [19]

Chan et al.

[11] Patent Number: 4,870,208
[45] Date of Patent: Sep. 26, 1989

[54] ASYMMETRIC HYDROGENOLYSIS OF EPOXIDES

[75] Inventors: Albert S. C. Chan, St. Louis; James P. Coleman, Maryland Heights; Grace M. Wagner, Webster Groves, all of Mo.

[73] Assignee: Monsanto Company, St. Louis, Mo.

[21] Appl. No.: 200,857

[22] Filed: Jun. 3, 1988

[51] Int. Cl.$^4$ .................... C07C 59/00; C07C 29/132
[52] U.S. Cl. ....................... 562/579; 560/60; 560/179; 560/180; 562/570; 562/582; 568/865; 568/866; 568/867
[58] Field of Search ............... 568/867, 902, 865, 866; 560/60, 179, 180; 562/570, 579, 582

[56] References Cited

U.S. PATENT DOCUMENTS

| | | | |
|---|---|---|---|
| 2,404,503 | 7/1946 | Kharasch et al. | 562/570 |
| 2,570,297 | 10/1951 | Weisbalt et al. | 562/570 |
| 2,831,891 | 4/1958 | Steadman | 562/582 |
| 2,939,880 | 6/1960 | Montagna et al. | 560/180 |
| 3,405,174 | 10/1968 | Sugerman | 562/579 |
| 3,463,813 | 8/1969 | Smith | 568/865 |
| 3,547,991 | 12/1970 | Schlossman | 562/582 |
| 3,975,449 | 8/1976 | Suzuki | 568/865 |
| 4,016,196 | 4/1977 | Kogure et al. | 560/60 |
| 4,329,487 | 5/1982 | Oritu et al. | 560/60 |
| 4,376,866 | 5/1983 | Englaender et al. | 560/60 |
| 4,409,395 | 10/1983 | Miyazaki et al. | 560/179 |
| 4,471,130 | 9/1984 | Katsuki et al. | 549/523 |
| 4,645,858 | 2/1987 | Lowrie et al. | 562/582 |
| 4,654,159 | 3/1987 | Bush et al. | 560/180 |
| 4,824,997 | 4/1989 | MacFarlane | 560/179 |

FOREIGN PATENT DOCUMENTS

| | | | |
|---|---|---|---|
| 46033 | 2/1982 | European Pat. Off. | |
| 0197766 | 3/1986 | European Pat. Off. | |
| 257967 | 3/1988 | European Pat. Off. | 568/867 |
| 2643400 | 3/1978 | Fed. Rep. of Germany | 568/867 |

OTHER PUBLICATIONS

Catalytic Hydrogenation of Epoxide with Tristriphenylphosphinerhodium Chloride, Mochida et al., Chemistry Letters (Japan), 10, 1025–1026 (1975).

Asymmetric Hydrogenation of β-Keto Carboxylic Esters, Noyori et al., Jour. Amer. Chemical Soc., 109, 5856–5858 (1987).

B. R. James, Adv. Organomet. Chem. Ser. (1979), 17, 319–405, Hydrogenation Reactions.

K. B. Sharpless et al., Pure & Appl. Chem., vol. 55, No. 4, 589–604 (1983), Stereo and Regioselective Openings of Chiral 2,3-Epoxy Alcohols.

Asymmetric Reactions, Takeuchi et al., Bull. Chem. Soc. (Japan), 57 (7), 1920–1928 (1984).

Primary Examiner—Werren B. Lone
Attorney, Agent, or Firm—Charles E. Smith; James W. Williams, Jr.; Arnold H. Cole

[57] ABSTRACT

A process of preparing chiral alcohols by the asymmetric catalytic hydrogenolysis of epoxides using rhodium or ruthenium catalysts containing chiral phosphine ligands.

10 Claims, No Drawings

ASYMMETRIC HYDROGENOLYSIS OF EPOXIDES

FIELD OF THE INVENTION

This invention relates to a process of preparing chiral alcohols by the asymmetric catalytic hydrogenolysis of epoxides using rhodium or ruthenium catalysts containing chiral phosphine ligands.

SUMMARY OF RELATED ART

Chiral alcohols are a class of chemicals used for the synthesis of natural products and drugs. Traditionally, these compounds are made either by fermentation or by means of cost-intensive resolution of racemic mixtures.

Non-traditional methods of preparing chiral alcohols are disclosed in B. R. James, Adv. Organomet. Chem. Ser., 1979, 17, 319 and R. Noyori et. al., J. Am. Chem. Soc., 1987, 109, 5856, which describe the synthesis of chiral alcohols from the asymmetric hydrogenation of prochiral ketones. K. B. Sharpless et. al., Pure and Appl. Chem., Vol. 55, No. 4, 589, 1983 disclose the hydrogenolysis of chiral epoxides with $LiAlH_4$ or $NaBH_4$ to make certain types of chiral alcohols.

None of the above references disclose the process of preparing chiral alcohols by the present process.

SUMMARY OF THE INVENTION

The present invention is a process to prepare chiral alcohols by the asymmetric hydrogenolysis of epoxides using rhodium or ruthenium catalysts containing chiral phosphine ligands.

DETAILED DESCRIPTION OF THE INVENTION

The present invention is illustrated by the following scheme:

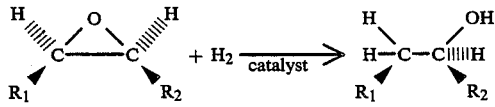

wherein $R_1$ is selected from hydrogen, alkyl, aryl and carboxyl-containing groups. $R_2$ is a carboxyl-containing group. Examples of $R_1$ include methyl, ethyl, propyl, phenyl, benzyl, carboxyl, carboxymethyl, carboxyethyl, carboxybutyl and their salts. Examples of $R_2$ include carboxyl, carboxyethyl, carboxymethyl, carboxybutyl and their salts.

The epoxide suitable for the present invention is any epoxide with at least one chiral center having a carboxyl-containing group. A preferred epoxide is of meso form which, upon asymmetric hydrogenolysis, produces one enantiomer of the chiral compound as a dominant species. Examples of suitable epoxides include cis-epoxysuccinic acid disodium salt, sodium 3-methyl-3-phenylglycidate, sodium 3-sec-butyl-3-methylglycidate, sodium 2,3-epoxybutyrate, 2,3-epoxy-3-(2-methoxyphenyl)propionic acid sodium salt, 2,3-epoxy-2,3-dimethylsuccinic acid disodium salt, 2,3-epoxy-1,4-butanedicarboxylic acid disodium salt, lithium 3-phenylglycidate and sodium glycidate, and other acid salts. When an essentially pure enantiomer of a non-symmetrical, chiral epoxide is used, the regiospecific hydrogenolysis can provide an essentially pure chiral alcohol product, e.g.,

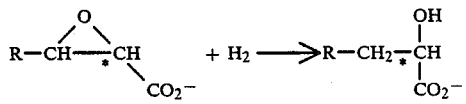

where * indicates a chiral center and R is hydrogen, alkyl, aryl or carbonyl-containing groups. When a racemic mixture of non-symmetrical epoxide is used, a racemic hydroxyl product is obtained at total conversion due to the retention of the chiral center, e.g.,

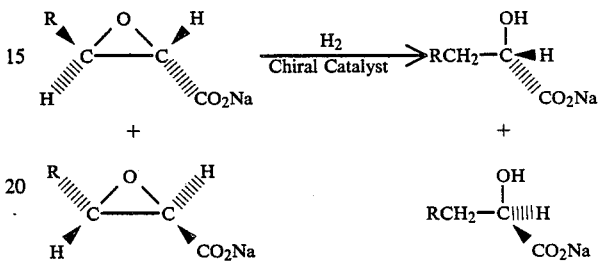

where R is defined above.

However, at partial conversion, one diastereomer of the starting material reacts faster than the other and a kinetic resolution can take place such that the product contains a dominant enantiomer, even though the starting material contains a 50/50 mixture of the two diastereomers.

The catalyst suitable for the present invention is any rhodium or ruthenium asymmetric hydrogenation catalyst containing a chiral phosphine ligand. Other noble metal asymmetric hydrogenation catalysts give little or no yield of the desired chiral hydroxyl compound. Suitable rhodium catalysts include catalysts of the structure Rh(diene)(chiral phosphine)A, where diene includes norbornadiene and cyclooctadiene or two molecules of alkenes such as ethylene. A is a counter ion, such as for example $BF_4$, $PF_6$, $ClO_4$, halides, pseudohalides and carboxylates. Chiral phosphines are phosphine ligands containing one or more chiral centers. Examples of suitable rhodium catalysts include [rhodium(1,5-cyclooctadiene)(R,R-1,2-ethanediylbis-(o-methoxyphenyl)phenylphosphine]tetrafluoroborate ([Rh(COD)(R,R-DIPAMP)]Bf4), [rhodium (2,5-norbornadiene)(R-1,2-bis(diphenylphosphino)cyclohexylethane]hexafluorophospate ([Rh(NBD)(R-Cycphos)]PF6), [rhodium(2,5-norbornadiene)(2R,3R-bis(diphenylphosphine)butane]perchlorate ([Rh(NBD)(R,R-Chiraphos)]ClO4), [rhodium(1,5-cyclooctadiene)(2R,3R-O-isopropylidene-2,3-dihydroxy-1,4-bis(diphenylphosphino)butane]tetrafluoroborate ([Rh(COD)(R,R-Diop)BF4), [rhodium(2,5-norbornadiene)(R-1,2-bis(diphenylphosphino)propane)]perchlorate ([Rh(R-Prophos)ClO4), [rhodium(2,5-norbornadiene)(R-1,2-bis(diphenylphosphino)phenylethane)]perchlorate ([Rh(NBD)(R-Phenphos)]ClO4), [rhodium(norbornadiene)((+)-2,3-O-Isopropylidene-2,3-dihydroxy-1,4-bis(diphenylphosphino)butane)]tetrafluoroborate, ([Rh(NBD)((+)-DIOP]BF4), [rhodium(-norbornadiene)((R)-α-[(s)-2,1'-Bis(diphenylphosphino)-ferrocenyl]ethyldimethylamine)]tetrafluoroborate, ([Rh(NBD)(BPPFA)]BF4), [rhodium(norbornadiene)(s,s)-2,4-bis(diphenylphosphino)pentane)]tetrafluoroborate, ([Rh(NBD)(skewphos)]BF4), [rhodium(-norbornadiene)((−)-N-t-Butoxycarbonyl-4-diphenylphosphino-2-diphenylphosphosphinomethylpyrrolidine)]tetrafluoroborate, ([Rh(NBD)(BPPM)]BF$_4$), chloro(norbornadiene)(N,N'-bis[(R)-α-methylbenzyl]-N,N'-bis(diphenylphosphino)ethylenediamine)rhodium, (Rh(NBD)(PNNP)Cl), [rhodium(norbornadiene)(trans-4,5-bis(5H-dibenzophospholylmethyl)-2,2-dimethyl-1,3-dioxolane)]tetrafluoroborate, ([Rh(NBD)(DIPHOL)]BF$_4$), chloro(norbornadiene)((R)-(+)-2,2'-bis(diphenylphosphino)-1,1'-binaphthyl)rhodium, (Rh(NBD)(R-BINAP)Cl), chloro(norbornadiene)((R)-2,3-bis(diphenylphosphino)propane)rhodium, (Rh(NBD)(R-PROPHOS)Cl), chloro((s,s)-2,3-bis(diphenylphosphino)butane)rhodium dimer, ([Rh(CHIRAPHOS)Cl]$_2$), [rhodium(cyclooctadiene)((R,R)-N-benzyl-3,4-bis(diphenylphosphino)-pyrrolidine)]tetrafluoroborate, ([Rh(COD)(N-Bz-pyrphos)]BF$_4$), [rhodium(norbornadiene)((R)-1,2-bis(diphenylphosphino)-cyclohexylethane)]tetrafluoroborate, ([Rh(NBD)(cycphos)]BF$_4$), chloro(norbornadiene)(N,N'-bis[(s)-α-(1-naphthyl)ethyl]-N,N'-bis(diphenylphosphino)ethylenediamine)rhodium, (Rh(NBD)((s)-naphthylethyl-PNNP)Cl), and dichlorotetrakis(dimethylsulfoxide)ruthenium+(s,s)-2,3-bis(diphenylphosphino)butane, (Ru(DMSO)$_4$Cl$_2$+-CHIRAPHOS). For the preparation of [Rh(R,R-Dipamp)(COD)]BF$_4$, see Vineyard, B. D., Knowles, W. S., Sabacky, M. J. Bachman, G. L. and Weinkauff, D. J., *J. Amer. Chem. Soc.*, 1977, 99, 5046. For the preparation of [Rh(Diop)(COD)]BF$_4$, see Kagan, H. B. and Dang, T. P., *J. Amer. Chem. Soc.*, 1972, 94, 6429. For the preparation of [Rh(R-Cycphos) NBD]PF$_6$, see Riley, D. P. and Shumate, R. E., *J. Org. Chem.*, 1980, 45, 5187. A detailed description of suitable catalysts for the present invention is disclosed in "Asymmetric Synthesis", Vol. 5, Ed. by James D. Morrison, Academic Press, Orlando (1985). The above references are hereby incorporated by reference.

The catalyst concentration is not critical and can vary widely depending on reaction conditions. The catalyst concentration can be in the range of $1 \times 10^{-6}$ to $5 \times 10^{-1}$M, a preferred concentration being in the range of about $1 \times 10^{-4}$ to $5 \times 10^{-2}$M. Higher catalyst concentrations increase the reaction rate. Excess catalyst has little or no adverse effect on the selectivity to the desired hydroxyl compounds.

The reaction temperature of the present invention is a temperature sufficient to initiate and sustain the reaction. The temperature can vary from sub-ambient temperature, (ambient being about 23° C.), to beyond the boiling point of the solvent system. A preferred reaction temperature is in the range of 0° C. to 100° C. Higher reaction temperatures increase the reaction rate. In the presence of water, higher reaction temperatures, e.g., 60° C. or higher, cause the hydrolysis of the epoxide, resulting in lower selectivity to the hydroxyl compound, while lower reaction temperatures, e.g., less than 20° C., decrease the reaction rate.

The reaction takes place in a solvent system suitable for solubilizing the catalyst and substrate, such as ethers, alcohols, nitriles, ketones and mixtures thereof. Examples of suitable solvents include water, tetrahydrofuran, methanol, acetonitrile and acetone. The amount of solvent present can vary widely. It is desirable to have sufficient solvent for the reaction system to be one phase. The solvent to substrate ratio can vary in the range of 1000:1 to 1:1, a preferred range being from 100:1 to 2:1.

The reaction pressure is atmospheric pressure or higher. A preferred range is from atmospheric (103 kPa), to about 3,000 psig (21,000 kPa), and a preferred range is from 20 psig (140 kPa) to 1000 psig (7000 kPa). When the solvent is an alcohol, the reaction can take place without an external H$_2$ source, since the solvent is a hydrogen source. It is preferred, however, to have an external source of hydrogen, e.g. H$_2$ gas, which increases the rate of reaction. The higher the H$_2$ pressure, the higher the reaction rate. The H$_2$ can be introduced to the reaction mass by any convenient means, such as pressurized sources, e.g., gas cylinders or pumps.

The reaction time is dependent upon catalyst concentration, substrate concentration, hydrogen pressure and reaction temperature. The reaction time ranges from about 5 minutes to about 150 h. Under reaction conditions where the reaction rate is relatively slow, it is advantageous to have a longer reaction time to favor higher conversions of the reactants. A preferred reaction time is from about 1 h to about 75 h.

The following examples are for illustrative purposes only and are not intended to limit the claimed invention in any manner.

EXAMPLES

Examples 1 through 17 were performed according to the following procedure: A 100 ml Fisher-Porter reaction bottle was charged with the substrate, cis-epoxysuccinic acid disodium salt, catalyst, and solvent system under a N$_2$ atmosphere. The bottle was pressurized with hydrogen gas as indicated, stirred and allowed to react. The crude product was obtained by evaporating the solvent. The % conversion was determined by NMR, and the enantiomer excess (e.e.) was determined by chiral GLC after derivatization. A method for GLC analysis of chiral alcohol compounds is disclosed by W. A. Konig et. al., J. Chromatogr., 1982, 238, 427.

TABLE 1

Asymmetric Hydrogenolysis of cis-Epoxysuccinic Acid Disodium Salt

| Ex. | Catalyst (mg) | Substrate (g) | Solvents (g) | Temp. (°C.) | $P_{H_2}$ (psig, kPa) | Reaction Time (h) | % Conversion | % e.e. |
|---|---|---|---|---|---|---|---|---|
| 1 | [Rh(NBD)((+)-DIOP]BF$_4$ (50) | 0.5 | H$_2$O/THF (10.5/14) | 60 | 80 | 72 | 100 | 25.8 (D) |
| 2 | [Rh(NBD)(BPPFA)]BF$_4$ (50) | 0.5 | H$_2$O/THF (6/13) | 60 | 80 | 14 | 100 | 10.2 (D) |
| 3 | [Rh(NBD)((+)-DIOP)]BF$_4$ (50) | 0.5 | H$_2$O/THF/CH$_3$OH (7.6/14/4) | 23 | 200 | 14 | 100 | 30.2 (D) |
| 4 | [Rh(NBD)(skewphos)]BF$_4$ (20) | 0.36 | H$_2$O/THF/CH$_3$OH (7.6/6/1.6) | 23 | 600 | 72 | 100 | 28.5 (D) |
| 5 | [Rh(NBD)(skewphos)]BF$_4$ (50) | 0.84 | H$_2$O/THF/CH$_3$OH (15.8/14/3.7) | 23 | 20 | 72 | 100 | 28 (D) |
| 6 | Rh(NBD)(PNNP)Cl (100) | 0.6 | D$_2$O/THF/CH$_3$OD (5/10/4) | 60 | 80 | 14 | 100 | 33.5 (D) |

TABLE 1-continued

Asymmetric Hydrogenolysis of cis-Epoxysuccinic Acid Disodium Salt

| Ex. | Catalyst (mg) | Substrate (g) | Solvents (g) | Temp. (°C.) | $P_{H_2}$ (psig, kPa) | Reaction Time (h) | % Conversion | % e.e. |
|---|---|---|---|---|---|---|---|---|
| 7 | Rh(NBD)(PNPP)Cl (50) | 0.67 | H$_2$O/THF/CH$_3$OH (6.5/4.5/4) | 25 | 80 | 14 | 100 | 37 (D) |
| 8 | [Rh(COD)(DIPAMP)]BF$_4$ (50) | 0.66 | H$_2$O/THF/CH$_3$OH (6.6/4.5/4) | 25 | 80 | 14 | 10 | 7 (L) |
| 9 | [Rh(NBD)(DIPHOL)]BF$_4$ (40) | 0.6 | H$_2$O/THF/CH$_3$OH (6.7/9.7/3.7) | 25 | 80 | 14 | 20 | 33 (L) |
| 10 | [Rh(NBD)(BPPM)]BF$_4$ (40) | 0.6 | H$_2$O/THF/CH$_3$OH (6.7/9.7/3.7) | 25 | 80 | 14 | 100 | 23.2 60 |
| 11 | Rh(NBD)(R-BINAP)Cl (120) | 0.8 | H$_2$O/CH$_3$OH (9/16) | 25 | 80 | 14 | 100 | 19.5 (L) |
| 12 | Rh(NBD)(R-PROPHOS)Cl (80) | 0.8 | H$_2$O/CH$_3$OH (9/16) | 25 | 80 | 14 | 100 | 17.6 (L) |
| 13 | [Rh(CHIRAPHOS)Cl]$_2$ (30) | 0.6 | H$_2$O/THF/CH$_3$OH (7.9/5.4/4.8) | 25 | 80 | 14 | 30 | 6 (D) |
| 14 | [Rh(NBD)(cycphos)]BF$_4$ (20) | 2.3 | H$_2$O/CH$_3$OH (6/13) | 60 | 60 | 14 | 100 | 23 (L) |
| 15 | [Rh(NBD)(+)-DIOP]BF$_4$ (50) | 0.37 | H$_2$O/CH$_3$OH | 25 | None | 124 | ~5 | 20 (D) |
| 16 | RuCl$_2$(DMSO)$_4$ + CHIRAPHOS (50) | 0.34 | H$_2$O/CH$_3$OH (7/11) | 60 | 80 | 14 | 100 | 23 (D) |
| 17 | Rh(NBD)((S)-Naphthyl-ethyl-PNNP)Cl | 0.2 | H$_2$O/CH$_3$OH (5/16) | 23 | 80 | 72 | 95 | 59 (L) |

We claim:

1. A process for preparing chiral alcohols comprising the asymmetric hydrogenolysis of a carboxy-containing chiral epoxide represented by the formula

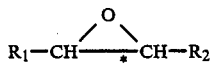

wherein * indicates a chiral center, R$_1$ represents hydrogen, alkyl, aryl and carboxyl-containing radicals and R$_2$ represents carboxyl-containing radicals, in the presence of rhodium or ruthenium catalysts containing chiral phosphine ligands.

2. The process of claim 1 wherein the rhodium or ruthenium catalyst containing chiral phosphine ligands is selected from ([Rh(NBD)((+)-DIOP]BF$_4$), ([Rh(NBD)(BPPFA)]BF$_4$), ([Rh(NBD)-(skewphos)]BF$_4$), [Rh(NBD)(BPPM)]BF$_4$, (Rh(NBD)-(PNNP)Cl), [Rh(NBD)(DIPHOL)]BF$_4$, (Rh(NBD)(R-BINAP)Cl), (Rh(NBD)(R-PROPHOS)Cl), [Rh(CHIRAPHOS)Cl]$_2$, [Rh-(COD)(N-Bz-pyrphos)]Bf$_4$, [Rh(NBD)(cycphos)]BF$_4$, Rh(NBD)((s)-naphthylethyl-PNNP)Cl, and (Ru(DMSO)$_4$Cl$_2$+-CHIRAPHOS).

3. The process of claim 2 wherein the epoxide is selected from the group comprising cis-epoxysuccinic acid, sodium 3-methyl-3-phenylglycidate, sodium 3-sec-butyl-3-methylglycidate, sodium 2,3-epoxybutyrate, 2,3-epoxy-3-(2-methoxyphenyl)propionic acid sodium salt, 2,3-epoxy-2,3-dimethylsuccinic acid disodium salt, 2,3-epoxy-1,4-butanedicarboxylic acid disodium salt, lithium 3-phenylglycidate and sodium glycidate, and other acid salts.

4. The process of claim 3 wherein the epoxide is of achiral meso form.

5. The process of claim 3 wherein the epoxide is a pure enantiomer of a non-symmetrical, chiral epoxide.

6. The process of claim 3 wherein the epoxide is a racemic mixture of a non-symmetrical epoxide.

7. The process of claim 2 wherein the catalyst concentration is in the range of $1 \times 10^{-6}$ to $5 \times 10^{-1}$M.

8. The process of claim 7 wherein the reaction temperature is in the range of 0° C. to 100° C.

9. The process of claim 8 wherein an external source of hydrogen consisting of H$_2$ gas is used.

10. A process to prepare chiral alcohols comprising the asymmetric hydrogenolysis of epoxides represented by the formula

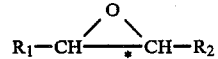

wherein * indicates a chiral center, R$_1$ represents hydrogen, alkyl, aryl and carboxyl-containing radicals and R$_2$ represents carboxyl-containing radicals, in the presence of rhodium or ruthenium catalysts containing chiral phosphine ligands wherein the rhodium or ruthenium catalysts are selected from ([Rh(NBD)-((+)-DIOP]BF$_4$), ([Rh(NBD)(BPPFA)]BF$_4$), ([Rh(NBD)-(skewphos)]BF$_4$), [Rh(NBD)(BPPM)]BF$_4$, (Rh(NBD)-(PNNP)Cl), [Rh(NBD)(DIPHOL)]BF$_4$, (Rh(NBD)(R-BINAP)Cl), (Rh(NBD)(R-PROPHOS)Cl), [Rh(CHIRAPHOS)Cl]$_2$, [Rh-(COD)(N-Bz-pyrphos)]BF$_4$, [Rh(NBD)(cycphos)]BF$_4$, Rh(NBD)((s)-naphthylethyl-PNNP)Cl, and (Ru(DMSO)$_4$Cl$_2$+-CHIRAPHOS, wherein the catalyst concentration is in the range of $1 \times 10^{-6}$ to $5 \times 10^{-1}$, wherein the reaction temperature is in the range of 0° C. to 100° C. and wherein an external source of hydrogen consisting of H$_2$ gas is used.

* * * * *